United States Patent [19]

Matsumoto

[11] Patent Number: 4,511,496

[45] Date of Patent: Apr. 16, 1985

[54] SLOW-RELEASE PERFUME COMPOSITIONS AND A PROCESS FOR THE PREPARATION OF THEM

[75] Inventor: Yuuichi Matsumoto, Abiko, Japan

[73] Assignee: Soda Aromatic Company, Limited, Tokyo, Japan

[21] Appl. No.: 504,226

[22] Filed: Jun. 14, 1983

[30] Foreign Application Priority Data

Jun. 22, 1982 [JP] Japan ................................ 57-106111

[51] Int. Cl.³ ............................................... A61K 7/46
[52] U.S. Cl. ............................................... 252/522 A
[58] Field of Search .................................... 252/522 A

[56] References Cited

U.S. PATENT DOCUMENTS 3,553,296 1/1971 Gaecket .......................... 252/522 A Primary Examiner—Anton H. Sutto
Attorney, Agent, or Firm—Scully, Scott, Murphy & Presser

[57] ABSTRACT

A pellet of ethylene-vinyl acetate copolymer and a perfume are mixed in a mixer, and when the perfume has been impregnated into only the surface layer portion of the pellet, then a fine powder is added and mixed with the perfume-impregnated pellet for the purpose of coating the surface thereof.

12 Claims, No Drawings

SLOW-RELEASE PERFUME COMPOSITIONS AND A PROCESS FOR THE PREPARATION OF THEM

BACKGROUND OF THE INVENTION

The present invention relates to slow-release perfume compositions and a process for the preparation of them. As those compositions supporting a perfume in a solid carriers, there are known so-called gel aromatic comprising water-soluble gels such as agar and carrageenan and perfumes dispersed therein, as well as perfumed resins comprising thermoplastic resins and perfumes incorporated therein.

But the former is disadvantageous in that the effective volatility is low or in that the water soluble gels result in limitation of the mode of use. The latter is also disadvantageous in that the perfume is easily deteriorated or the preparing process is available only for limited kinds of perfume, because of mixing a thermoplastic resin with a perfume at its melting temperature. In view of these defects, methods of impregnating a thermoplastic resin with a perfume at near room temperatures have come to be adopted recently. But many of them have some defects, for example, the impregnating process usually takes a long time and the obtained resin pellets adhere to each other to give the cluster of pellets during storage or the releasing volatility of a perfume is not so sufficient as to be acceptable for perfume products. Therefore, it has been desired to develop more improved compositions and a more improved manufacturing process of them.

SUMMARY OF THE INVENTION

It is an object of the present invention to provide novel slow-release perfume compositions which have a superior effect to release perfume gradually from the solid carrier. And it is another object to provide a novel process which has the advantage of preparing such perfume compositions for a brief time at low temperatures and to avoid adhesion of resin pellets during storage.

The slow-release perfume compositions of the present are obtained by impregnating the surface of ethylene-vinyl acetate copolymer pellet with the desirable amount of perfume, then by coating the pellet with the fine powder which is insoluble in the pellet and the perfume, using a mixer or a blender and having sufficient volatility to release the perfume as gradually as to be acceptable for perfume products.

DESCRIPTION OF THE PREFERRED EMBODIMENTS

The ethylene-vinyl acetate copolymer (hereinafter referred to simply as "EVA") used as a carrier resin in the pesent invention if of a vinyl acetate content ranging from 19% to 40%, preferably 25% to 33%, by weight. The EVA is used in the form of a pellet, which is preferably in the shape of a sphere or cylinder having a particle size in the range of about 1 to 10 mm, preferably about 2 to 6 mm. But the pellet may take other forms.

Preferably, the perfume used in the present invention contains hydrocarbons and/or esters as an essential component. Examples of hydrocarbons include monoterpene hydrocarbons such as limonene, $\alpha$-pinene and $\beta$-pinene; sesquiterpene hydrocarbons such as caryophyllene, santalene, thujopsene and cedrene; diterpene hydrocarbons such as abietin and camphorene; and aromatic hydrocarbons such as p-cymene and styrene. Examples of esters include aliphatic and aromatic esters having usually not more than 20, preferably not more than 15, carbon atoms, such as, for example, isoamyl acetate, geranyl acetate, citronellyl acetate, linalyl acetate, benzyl acetate, benzyl benzoate, benzyl salicylate, cinnamyl cinnamate, and isoamyl undecylenate. The perfume used in the present invention is usually a compound perfume, and it is desirable that not less than 30%, preferably not less than 50%, by weight of all the perfume components is occupied by the hydrocarbons and/or esters as exemplified above.

The EVA pellet is impregnated with perfume under rotation in a mixer such as a drum mixer, a V type blender, or a conical blender which are generally used for the powder. The perfume is used in an amount ranging usually from 10% to 40%, preferably from 25% to 35%, by weight based on the weight of the composition. Total amount of the perfume may be added at the beginning, or alternatively may be added gradually in a continuous manner. Impregnating operation is completed preferably at a temperature in the range of about 10° to 50° C.

Under the conditions described above the fine powder must be added into the mixer at the time when the perfume has been impregnated almost completely just onto the surface of pellets and not penetrated to the core of the pellets.

The state of impregnating the perfume into the surface of the pellet can be easily observed by measuring the coloring thickness on the surface of a transversely cut piece of a pellet with a specially colored perfume at any stage of the process. The thickness of the perfume-impregnated surface of the pellet at the time of adding the fine powder, is desirably not to be larger than 30%, preferably not to be larger than 15% of the diameter of a transverse section in the longitudinal axis direction (in any axial direction in the case of a sphere) of the pellet, measured from the outer edge of the cut pellet.

At this thickness the appearance of the surface of the pellet is no longer wet. According to the present invention the adding or a mixing of a fine powder with the perfume impregnated pellet has to be done at the stage described above, and the pellets are coated finely with a fine powder. Finally the high quality products can be obtained in a short time.

Many kinds of fine powders as a coating material may be used, if they possess properties such as superior lubricity, insolubility in the pellet and the perfume and not being hygroscopic. Considering that the perfume impregnated EVA pellet of the present invention provides an excellent use as a houshold item, it is desirable to use a fine powder conforming to the Cosmetic Material Standard (JAPAN) or one comparable thereto.

The fine powder coating method is easy, but includes extremely important objects in the present invention. Explaining the details of the coating process, a desirable amount of the fine powder is added to the perfume impregnated pellet of EVA in a mixer, the surface of the pellet is still viscous in a soft, swollen and wet state, and then the mixing is continued for about 15 to 30 minutes, until there is obtained the final product being coated perfectly and uniformly. This coating method unlike the so-called "sprinkled powder" means that the coated powder never fails off from the pellet not only just after its formation but also when the pellet surface become dry, and that the impregnated perfume on the surface will gradually penetrate and difuse reaching to the core of the pellet. For these reasons, during the subsequent stage of the coating there isn't a possibility at all such as preventing the progress of the coating by the exposure of the viscous surface of pellets due to the falling of the coated powder, and at every time for consumer use the final product there isn't a probability at all such as scattering the powder from the container of it.

As the fine powder for coating there may be used both organic and inorganic fine powders, of which the latter is generally preferred. Examples of the coating fine powder include those which can be used as perfume carriers or lubricants, such as silicic acid anhydride, magnesium silicate, aluminum silicate, calcium silicate, stearic acid, zinc stearate, aluminum stearate, magnesium stearate, Carbowax 6000 and talc, as well as those which can be used as pigments, such as titanium oxide, kaolin, zinc oxide, magnesium carbonate, calcium carbonate and mica. The particle size of these fine powders is not specially limited; for example, they may range from 200 to 300 mesh. The amount of the fine powder to be added may range from an amount sufficient to coat the pellet surface to a large excess amount, but usually an amount of about 0.3 to 1% by weight is enough. The pellets thus coated with the fine powder can immediately be subdivided and charged into final product containers or charged into a wide-mouthed drum or the like for bulk transit. During storage of the pellet in a closed container after such operations, the perfume which has been impregnated into the surface layer portion will penetrate and diffuse uniformly reaching to the core portion of the pellet to provide a final perfume composition.

In case the fine powder coating is not applied to the perfume-impregnated pellet, the rotational mixing operation takes an extremely long time for the perfume impregnation in order to obtain pellets capable of withstanding the subdividing and charging operation into final product containers or the charging operation into a wide-mouthed drum or the like for bulk transit. But, by adopting the process of the present invention, the rotational mixing operation can be done in much shorter time; besides, the slow-release effect of the resultant product is improved.

The thus-obtained slow-release perfume composition of the present invention exhibits a moderate releasing velocity in various modes of use, for example, by inserting it into a toilet paper supporting core which communicates with the exterior through its hollow portion.

The following examples are given to further illustrate the invention.

EXAMPLE 1

125 kg. (65 parts) of EVA resin pellets "ULTRATHENE UE-750" (vinyl acetate content: 32%, a product of Toyo Soda Manufacturing Co.) and 67 kg. (35 parts) of a lemon like perfume containing 35% of hydrocarbons were charged into a drum type rotary mixer having a capacity of 500 liters, which was rotated for 7 hours at a room temperature of 15° C. and at a linear velocity of 34 cm/sec. At the end of this operation, the pellet surfaces were no longer in a wet state, and their rolling state resembled that of EVA pellets alone containing no perfume. At this time, a sample pellet dyed in deep blue was taken out from a testing, drum type rotary mixer which had been operated for the same period of time under the same conditions but at a 1/20 scale (drum capacity: 25 liters, pellet feed: 6.25 kg., perfume feed: 3.35 kg.) using the above perfume after coloration in deep blue, and was cut transversely through its central part. The cut piece, when observed and measured, proved to have a diameter of 5 mm and be colored by penetration of the perfume at a thickness of 0.8 mm from the outer edge, from which it was confirmed that a selective penetration of the perfume into the surface layer had been completed.

Then, 1.92 kg. (1 wt.% of the feed) of a fine powder of talc (conforming to the Cosmetics Material Standard) which had passed through 300 mesh sieve was added and the mixing was continued under rotation for 30 minutes at the same linear velocity. As a result, the impregnated pellet surfaces which initially had an impression of a sprinkled powder resumed the original gloss, and the rolling state of the pellets became extremely smooth like that of pellets containing no perfume. Therefore, it was assumed that the talc coating was completed to a satisfactory extent, and the rotation was stopped to obtain the product. The talc-coated, lemon perfume-impregnated pellets thus obtained were fed to an automatic filling apparatus for final product containers; as a result, the apparatus could be operated extremely smoothly without clogging at all the hopper and nozzle portions. Separately, the pellets were charged into a wide-mouthed drum can having a capacity of 200 liters, and after storage for one month, the can was opened; as a result, it was found that there had been formed only a very fragile block, which was easily disintegrated by lightly shaking only the bottom portion of the can.

On the other hand, perfume-impregnated pellets not coated with the fine powder of talc were also prepared simultaneously under the same time period and same conditions except that the mixing under rotation was continued for additional 7 hours after termination of the impregnation on the surface and hence continued for a total of 14 hours. When the uncoated pellets were fed to an automatic filling apparatus for final product containers, clogging occurred frequently resulting in discontinuance of the operation, while those which had been charged into a wide-mouthed drum can and stored for 10 days underwent blocking throughout the pellets, and particularly at a portion near the bottom there was formed a hard block which had to be struck strongly for disintegration. Further, a perfume volatilization test was conducted over a period of 30 days for comparison between the talc-coated, lemon perfume-impregnated pellets and the pellets not coated with the fine powder of talc (hereinafter referred to as uncoated pellets). As a result, the fine powder coating neither impeded perfume volatilization nor led to lowering of the volatility, but rather the volatilizing behavior of the uncoated pellets such that a large amount of perfume volatilizes during the initial four or five days and then the amount of volatilized perfume decreases gradually—which is a property common to various mixed perfumes comprising many components of different boiling points and various carriers impregnated with such mixed perfumes, including EVA resin after impregnation—was somewhat modified and a better slow-release effect was exhibited. The details are as shown in Table 1 below.

TABLE 1

|  | Coated Pellets | Uncoated Pellets |
| --- | --- | --- |
| Volatilized Amount during |  |  |
| 1st to 3rd day | 1.000 g. | 1.127 g. |

TABLE 1-continued

| | Coated Pellets | Uncoated Pellets |
|---|---|---|
| 4th to 6th day | 0.452 | 0.445 |
| 7th to 9th day | 0.272 | 0.281 |
| 10th to 12th day | 0.242 | 0.211 |
| 13th to 15th day | 0.166 | 0.149 |
| 16th to 18th day | 0.147 | 0.140 |
| 19th to 21st day | 0.164 | 0.156 |
| 22nd to 24th day | 0.099 | 0.094 |
| 25th to 27th day | 0.085 | 0.076 |
| 28th to 30th day | 0.062 | 0.048 |
| Total: | 2.689 g. | 2.727 g. |
| Volatility | 76.82% | 77.91% |

$$\left(\frac{\text{Total volatilized amount}}{\text{Perfume content}}\right)$$

Note: The test was carried out in such a manner that the two kinds of pellets were each placed exactly 10 g. (perfume content: 3.5 g.) into a scale in the open and were allowed to stand in a room kept at 15° C., and at every third day the weight was measured to calculated the volatilized amount during that period.

EXAMPLE 2

125 kg. (70 parts) of EVA resin pellets "ULTRATHENE UE-750" (vinyl acetate content: 32%, a product of Toyo Soda Manufacturing Co.) and 54 kg. (30 parts) of a fragrant olive like perfume containing 30% of esters were charged into a drum type rotary mixer having a capacity of 500 liters, which was rotated for 7 hours at a room temperature of 15° C. and at a linear velocity of 34 cm/sec. As a result, there were shown signs of termination of a selective surface layer impregnation such as that described in Example 1. At this time, a sample pellet in deep blue was taken out from a testing rotary mixer of a 1/20 scale which had been rotated for mixing simultaneously under the same time period and same conditions as in Example 1, and was cut transversely through its central part. The cut piece, when observed and measured, proved to have a diameter of 5.5 mm and a thickness of colored portion or perfume-penetrated portion of 0.6 mm from the outer edge. Then, 1.79 kg. (1 wt.% of the feed) of a fine powder of Carbowax 6000 (conforming to the Cosmetics Material Standard) which had passed through 300 mesh sieve after re-pulverization of coarse powder was added and the mixing was continued under rotation for 30 minutes at the same linear velocity to obtain product coated with the said fine powder. Then, in the same way as in Example 1, this product was charged to an automatic filling apparatus for final product containers and also into a wide-mouthed drum can for a 30 days storage test, and the effect of the coating was checked, which was as good as the coating effect attained in Example 1.

For comparison, uncoated pellets were also prepared simultaneously under the same time period and same conditions except that the mixing under rotation was continued for additional 8 hours after termination of the selective surface layer impregnation and hence continued for a total of 15 hours. This notwithstanding, it was impossible for the automatic filling apparatus to operate smoothly, and a hard block was formed during storage in a wide-mouthed drum.

Furthermore, a perfume volatilization test was carried out over a period of 30 days with respect to both the coated and uncoated pellets; as a result, the coated pellets exhibited a better slow-release effect, which result is just the same as Example 1. The details are as shown in Table 2 below.

| | Coated Pellets | Uncoated Pellets |
|---|---|---|
| Volatilized Amount during | | |
| 1st to 3rd day | 1.000 g. | 1.127 g. |
| 4th to 6th day | 0.374 | 0.364 |
| 7th to 9th day | 0.231 | 0.232 |
| 10th to 12th day | 0.213 | 0.196 |
| 13th to 15th day | 0.150 | 0.136 |
| 16th to 18th day | 0.137 | 0.129 |
| 19th to 21th day | 0.145 | 0.140 |
| 22nd to 24th day | 0.102 | 0.104 |
| 25th to 27th day | 0.081 | 0.070 |
| 28th to 30th day | 0.062 | 0.062 |
| TOTAL | 2.233 g. | 2.230 g. |
| Volatility | 74.43% | 74.33% |

$$\left(\frac{\text{Total volatilized amount}}{\text{Perfume content}}\right)$$

Note: The test was conducted in such a manner that the two kinds of pellets were each placed exactly 10 g. (perfume content: 3 g.) into a scale in the open and were allowed to stand in a room kept at 15° C., and at every third day the weight was measured to calculate the volatilized amount during that period.

EXAMPLE 3

125 kg. (70 parts) of EVA resin pellets "ULTRATHENE UE-750" (vinyl acetate content: 32%, a product of Toyo Soda Manufacturing Co.) and 54 kg. (30 parts) of a mixed lemon like perfume containing 35% of hydrocarbons were mixed by rotation using the same apparatus and under the same conditions as in Examples 1 and 2. The selective surface layer impregnation was completed in 5 hours. The thickness of the perfume penetrated portion proved to be 0.5 mm for a diameter of 5 mm when observed and measured using a transversely cut piece of a colored sample which had been prepared at a 1/20 scale in the same manner as in Examples 1 and 2. At this time, 1.79 kg. (1 wt.% of the feed) of a fine powder of titanium oxide which passed through 300 mesh sieve was added and the mixing was continued under rotation for 30 minutes to obtain product coated with titanium oxide. Because titanium oxide used as the coating agent is a white pigment, the coated pellets thus obtained were somewhat more whity opaque pellets in external appearance than in the cases of Examples 1 and 2. But, the results of application to the automatic filling step, of the filling and storage test using a wide-mouthed drum can and of the volatilization test for comparison with uncoated pellets, were all extremely superior just as in Examples 1 and 2.

EXAMPLE 4

125 kg. (70 parts) of "ULTRATHENE UE-750" (a product of Toyo Soda Manufacturing Co.) and 54 kg. (30 parts) of a olive like perfume were mixed by rotation using the same apparatus and under the same conditions as in Examples 1 through 3. The selective surface layer impregnation was completed in 7 hours. The pellets thus impregnated with the perfume were divided equally and charged 89 kg. each into two such apparatus, into one of which was then added 0.267 kg. (0.3 wt.%) of a fine powder of calcium silicate and into the other was added 0.89 kg. (1 wt.%) of a fine powder of magnesium stearate, and the mixing was continued for 30 minues under rotation in each of the apparatus to obtain pellets coated with the fine powder of calcium silicate and pellets coated with the fine powder of magnesium stearate.

The two kinds of pellets thus obtained were subjected to the automatic filling test, the filling and storage test using a wide-mouthed drum can and the volatilization test for comparison with uncoated pellets, the results of which were all satisfactory as in Examples 1 through 3.

What is claimed is:

1. A slow-release perfume composition comprising a pellet of an ethylene-vinyl acetate copolymer having a vinyl acetate content in the range of from 19 to 40% by weight, said pellet having a particle size in the range of about 1 to 10 mm, said pellet being impregnated with a perfume, said perfume containing as an essential component at least one fragrant component selected from the group consisting of hydrocarbons and esters, a fine powder being coated over the surface of said perfume-impregnated pellet and being present in an amount sufficient to coat the pellet surface thereof, and said fine powder being insoluble in either said pellet or said perfume.

2. The composition of claim 1, wherein said fine powder is an inorganic fine powder and is present in an amount of about 0.3 to 1% by weight.

3. The composition of claim 1, wherein the fine powder is selected from the group consisting of silicic acid anhydride, magnesium silicate, aluminum silicate, calcium silicate, stearic acid, zinc stearate, aluminum stearate, magnesium silicate, Carbowax 6000, talc, titanium oxide, kaolin, zinc oxide, magnesium carbonate, calcium carbonate and mica.

4. The composition of claim 1, wherein the particle size of the fine powder is in the range of 200 to 300 mesh.

5. The composition of claim 1, wherein the amount of perfume is in the range of 10 to 40% by weight based on the weight of said composition.

6. A process for preparing a slow-release perfume composition, which process comprises mixing a pellet of an ethylene-vinyl acetate copolymer having a vinyl acetate content in the range of 19% to 40% by weight, the particle size of said pellet being in the range of about 1 to 10 mm with a perfume containing as an essential component at least one fragrant component selected from the group consisting of hydrocarbons and esters, in a mixer to impregnate said pellet with said perfume into only a surface layer of said pellet, adding a fine powder in an amount sufficient to coat the pellet surface thereof, said fine powder being insoluble in either said pellet or said perfume, and mixing said fine powder with said perfume-impregnated pellet to coat the surface of said pellet with said fine powder.

7. The process of claim 4, wherein the amount of said perfume is in the range of 10 to 40% by weight based on the weight of said composition.

8. The process of claim 4, wherein the operation for mixing said pellet with said perfume is performed at a temperature in the range of 10° to 50° C.

9. The process of claim 6, wherein said fine powder is an inorganic fine powder and is present in an amount of about 0.3 to 1% by weight.

10. The process of claim 6, wherein the fine powder is selected from the group consisting of silicic acid anhydride, magnesium silicate, aluminum silicate, calcium silicate, stearic acid, zinc stearate, aluminum stearate, magnesium silicate, Carbowax 6000, talc, titanium oxide, kaolin, zinc oxide, magnesium carbonate, calcium carbonate and mica.

11. The process of claim 6, wherein the particle size of the fine powder is in the range of 200 to 300 mesh.

12. The process of claim 6, wherein the thickness of the perfume-impregnated surface of the pellet at the time of adding said fine powder is not larger than 30% of the diameter of a transverse section in the longitudinal axis direction of the pellet measured from the outer edge of a cut pellet.

* * * * *

UNITED STATES PATENT AND TRADEMARK OFFICE
CERTIFICATE OF CORRECTION

PATENT NO. : 4,511,496

DATED : April 16, 1985

INVENTOR(S) : Yuuichi Matsumoto

It is certified that error appears in the above-identified patent and that said Letters Patent are hereby corrected as shown below:

Column 1, line 44, after "present" insert --invention--.

Column 2, line 66, "fails" should be --falls--.

Column 6, line 6 "Coated Pellets 1st to 3rd day 1.000g
Uncoated Pellets 1.127g" should be
--Coated Pellets 1st to 3rd day 0.738g
Uncoated Pellets 0.797g--.

Signed and Sealed this

Tenth Day of September 1985

[SEAL]

Attest:

DONALD J. QUIGG

Attesting Officer     Acting Commissioner of Patents and Trademarks - Designate